United States Patent [19]

Urbach et al.

[11] 3,969,439

[45] July 13, 1976

[54] DITHIOPHOSPHORIC ESTERS

[75] Inventors: Hans Urbach, Lampertheim; Heinrich Adolphi, Limburgerhof, both of Germany

[73] Assignee: Badische Anilin- & Soda-Fabrik Aktiengesellschaft, Ludwigshafen (Rhine), Germany

[22] Filed: May 1, 1970

[21] Appl. No.: 33,884

[30] Foreign Application Priority Data

May 7, 1969  Germany............................ 1923269

[52] U.S. Cl............................. 260/942; 260/243 R; 260/247.1 B; 260/923; 260/943; 424/200; 424/212
[51] Int. Cl.² ...................... C07F 9/165; A01N 9/36
[58] Field of Search ..................................... 260/942

[56] References Cited

UNITED STATES PATENTS 3,431,325   3/1969   Greenbaum ................... 260/942 X

OTHER PUBLICATIONS

Mandel'baum et al., "Chem. Abs.," vol. 68, (1968), 29230q.
Mandel'baum et al., "Chem. Abs.," vol. 68, (1968), 86790w.

*Primary Examiner*—Anton H. Sutto
*Attorney, Agent, or Firm*—Johnston, Keil, Thompson & Shurtleff

[57] ABSTRACT

New and valuable dithiophosphoric esters which have a strong insecticidal and acaricidal action, and a process for controlling pests with these compounds.

2 Claims, No Drawings

DITHIOPHOSPHORIC ESTERS

The invention relates to new and valuable insecticidal dithiophosphoric esters and to agents for controlling pests, particularly insects.

It is known to use substituted phosphoric esters for controlling pests; however, their action in many cases is not satisfactory.

We have now found that dithiophosphoric esters having the formula

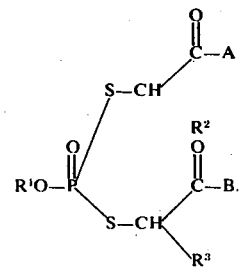

where
$R^1$ denotes an alkyl radical having 1 to 4 carbon atoms, A denotes the radicals $-OR^4$, $NH_2$, $-NHR^5$,

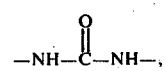

or $-NH-NH_2$, $R^4$, $R^5$, $R^6$ and $R^7$ each denoting an alkyl radical having 1 to 4 carbon atoms (methyl, ethyl, isopropyl, tert-butyl) or an alkenyl radical (propenyl), $R^6$ and $R^7$, together with the nitrogen atom whose substituents they are, may also denote a morpholine ring, and $R^5$ and $R^7$ may additionally denote an acyl radical having 1 to 3 carbon atoms (formyl, acetyl) or a radical having the formula $-CO-NH_2$, $-CO-NHR^8$ or $-CO-OR^8$, $R^8$ having the same meanings as $R^4$, $R^8$ and $R^4$ being identical or different, B has the same meanings as A, A and B being identical or different, $R^2$ denotes hydrogen, the methyl radical, an alkoxymethyl radical (methoxymethyl) or the radical

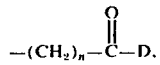

D having the same meanings as A, A and D being identical or different, n denoting one of the integers 0, 1 and 2, and A and D together denoting the radical $$-NH-\overset{\overset{O}{\|}}{C}-NH-,$$

and $R^3$ has the same meanings as $R^2$, $R^2$ and $R^3$ being identical or different, have a good action on pests, particularly insects, and spinning mites, e.g. aphides, houseflies, gnats, cockroaches, animal lice, nutes and parasitic flies, for instance in vegetable, fruit and ornamental crops, and on pests in the veterinary and domestic field.

The new dithiophosphoric esters may be prepared for instance by reacting salts of O-alkyl-S-carbalkoxymethyldithiophosphoric acids having the formula

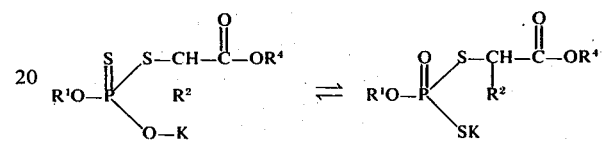

$R^1$, $R^2$ and $R^4$ having the meanings given above, and K denoting a cation, with α-halocarboxylic acid derivatives in accordance with the following equation:

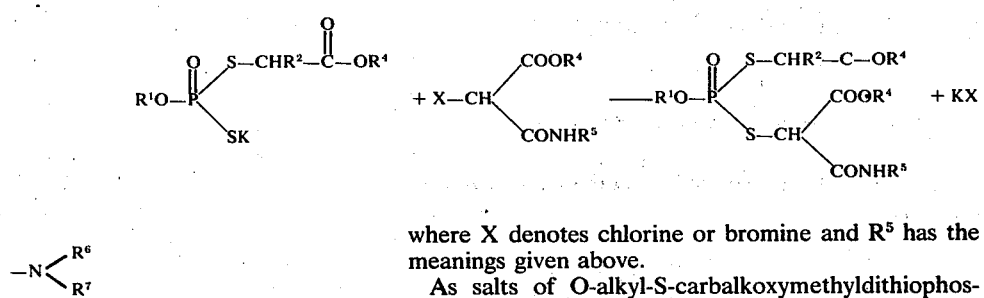

where X denotes chlorine or bromine and $R^5$ has the meanings given above.

As salts of O-alkyl-S-carbalkoxymethyldithiophosphoric acids, compounds may be used which are obtained from known insecticidal O,O-dialkyl-S-alkyldithiophosphoric esters by reaction with nucleophilic compounds, e.g. the following compound:

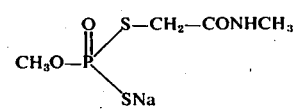

which is obtained by reacting the appropriate dithiophosphoric ester with, for example, sodium ethyl mercaptide in accordance with the following equation:

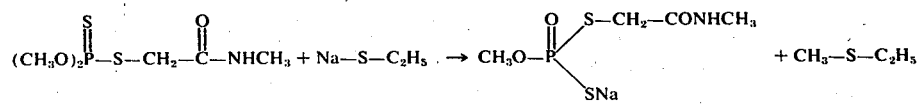

Suitable α-halocarboxylic acid derivatives are for example: the esters and amides of α-chloroacetic acid and bromomalonic acid.

It is also possible to synthesize the new dithiophosphoric esters by (possibly stepwise) reaction of O-alkyl-phosphoryl halides with the alkali metal salts of α-mercaptocarboxylic acid derivatives in accordance with the following equation:

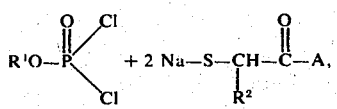

R[1], R[2] and A having the meanings given above.

Suitable O-alkylphosphoryl halides are: O-methylphosphoryl chloride, O-ethylphosphoryl chloride, and the corresponding bromides.

Suitable alkali metal salts of α-mercaptocarboxylic acid derivatives are for example: the sodium salts of thioglycolic esters or mercaptomalonic esters.

A further possibility for synthesis is the conversion of a new dithiophosphoric ester according to this invention into another one. Thus, for instance, the new dithiophosphoric ester

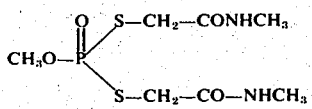

The preparation of the new dithiophosphoric esters is illustrated by way of the following examples.

EXAMPLE 1

Preparation of the compound

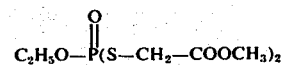

11.8 parts by weight of the compound having the formula

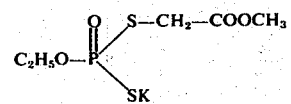

is dissolved in 200 parts of water. At 40°C, 4.3 parts of methyl chloroacetate is added and the mixture stirred for 3 hours at 50°C. After cooling, extraction is carried out twice, each time with 100 parts of chloroform, the chloroform extracts are combined and washed twice, each time with 100 parts of water. The chloroform solution is dried with anhydrous sodium sulfate and the chloroform evaporated off in vacuo (in the final stage at a pressure of about 1 mm); 8 parts of a yellow oil which is the compound having the above formula and the refractive index $n_D^{20} = 1.4999$ is obtained.

EXAMPLE 2

Preparation of the compound

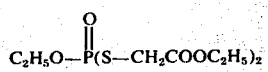

At 25° to 30°C, a suspension of 14 parts (by weight) of the sodium salt of ethyl thioglycolate in 250 parts of absolute ether is dripped into a solution of 8 parts of O-ethylphosphoryl chloride in 80 parts of absolute ether. The mixture is boiled for 90 minutes under reflux and washed after cooling with 250 parts of water, 250 parts of a 1% (by weight) aqueous sodium bicarbonate solution and again with 250 parts of water. The ether solution is dried with anhydrous sodium sulfate and the ether distilled off in vacuo. 8 parts of a yellow oil is obtained which is the compound having the above formula and the following refractive index: $n_D^{20} = 1.4946$.

Decomposition occurs when attempting distillation in a high vacuum.

The following table lists other new dithiophosphoric esters according to the invention which are prepared by one of the above-mentioned methods and which are designated by the meanings of the different substituents according to the formula

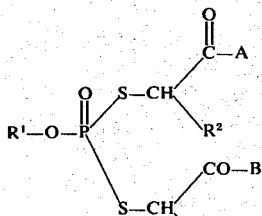

| No | R[1] | R[2] | R[3] | A | B | $n_D^{20}$ or m.p. |
|----|------|------|------|-----|-----|---------------|
| 1 | C₂H₅ | H | H | OCH₃ | OCH₃ | 1.4999 |
| 2 | C₂H₅ | H | H | OC₂H₅ | OC₂H₅ | 1.4949 |
| 3 | C₂H₅ | H | H | OCH₃ | OC₂H₅ | 1.4996 |
| 4 | CH₃ | H | H | OCH₃ | NHCH₃ | 1.5056 |
| 5 | C₂H₅ | H | H | OCH₃ | NHCH₃ | 1.5297 |
| 6 | CH₃ | COOC₂H₅ | COOCH₃ | OCH₃ | OC₂H₅ | 1.4866 |
| 7 | CH₃ | COOC₂H₅ | COOCH₃ | NHCH₃ | OCH₃ | 1.4982 |
| 8 | CH₃ | H | COOCH₃ | NHCH₃ | NHCH₃ | 135°C |
| 9 | CH₃ | H | COOC₂H₅ | NHCH₃ | NHCH₃ | 1.5214 |
| 10 | C₂H₅ | H | COOC₂H₅ | NHCH₃ | OC₂H₅ | 1.5429 |
| 11 | C₂H₅ | H | COOCH₃ | NHCH₃ | OCH₃ | 1.4887 |
| 12 | C₂H₅ | H | COOCH₃ | NHCH₃ | NHCH₃ | 65°C |
| 13 | CH₃ | H | CONHCH₃ | OCH₃ | OCH₃ | 1.5139 |
| 14 | CH₃ | H | COOC₂H₅ | OCH₃ | NHCH₃ | 1.4934 |
| 15 | C₂H₅ | H | CONHCH₃ | OC₂H₅ | NHCH₃ | 1.5082 |
| 16 | CH₃ | H | CONHCH₃ | NHCH₃ | NHCH₃ | 1.5199 |
| 17 | C₂H₅ | H | H | NHCH₃ | NH₂ | 1.5352 |
| 18 | CH₃ | H | H | NHCH₃ | NH₂ | 1.5383 |
| 19 | C₂H₅ | H | CONH₂ | NHCH₃ | NH₂ | 1.4870 |
| 20 | C₂H₅ | H | H | NHCH₃ | NH—CH₂—CH=CH₂ | 1.5215 |

-continued

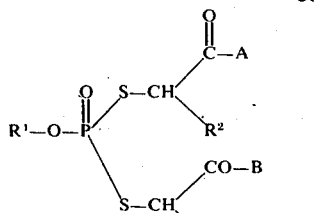

| No | R¹ | R² | R³ | A | B | $n_D^{20}$ or m.p. |
|---|---|---|---|---|---|---|
| 21 | C₂H₅ | H | H | NHCH₃ | NH—C(CH₃)₃ | — |
| 22 | C₂H₅ | H | CH₂O—CH₃ | NHCH₃ | —O—CH₃ | 1.5065 |
| 23 | CH₃ | H | CH₃ | NHCH₃ | —O—CH₃ | 1.5141 |
| 24 | C₂H₅ | H | CH₃ | NHCH₃ | —O—CH₃ | 1.5308 |
| 25 | CH₃ | H | CH₃ | NHCH₃ | —O—C₂H₅ | 1.4831 |
| 26 | C₂H₅ | H | CH₃ | NHCH₃ | —O—C₂H₅ | 1.5091 |
| 27 | C₂H₅ | H | CH₃ | NHCH₃ | NHCH₃ | 1.5181 |
| 28 | CH₃ | H | H | NHCH₃ | —O-iC₃H₇ | 1.5280 |
| 29 | C₂H₅ | H | H | NHCH₃ | —O,C₃H₇ | 1.5163 |
| 30 | C₂H₅ | H | H | CH=CH₂ NH—CH₂ | —O—C₂H₅ | 1.5082 |
| 31 | CH₃ | H | H | NHCH₃ | —NHCONH₂ | 1.4859 |
| 32 | C₂H₅ | H | H | NHCH₃ | NHCOCH₃ | 1.5261 |
| 33 | C₂H₅ | H | H | NHCH₃ | NHCONH₂ | — |
| 34 | C₂H₅ | H | H | NHCH₃ | NHCONHCH₃ | — |
| 35 | C₂H₅ | H | H | NHCH₃ | NHCOO—C₂H₅ | — |
| 36 | C₂H₅ | H | H | —O—CH₃ | NHCONH₂ | — |
| 37 | C₂H₅ | H | H | —O—CH₃ | N(CH₃)(COH) | 1.5056 |
| 38 | C₂H₅ | H | H | —O—C₂H₅ | —N(CH₃)(COH) | 1.5058 |

| No | Structure | $n_D^{20}$ or m.p. |
|---|---|---|
| 39 | C₂H₅—O—P(=O)(S—CH₂—COO—CH₃)(S—CH₂—CO—N⟨morpholine⟩) | 1.5314 |
| 40 | CH₃—O—P(=O)(S—CH₂—CO—NH—CH₃)(S—CH⟨C(=O)—N—S=O, C(=O)—N—H⟩) | 1.5462 |
| 41 | C₂H₅—O—P(=O)(S—CH₂—CO—NH—CH₃)(S—CH⟨C(=O)—N—C=O, S—N—H, =O⟩) | 1.5477 |

The agents according to the invention may be used as solutions, emulsions, suspensions or dusts. The form of application depends entirely on the purpose for which the agents are being used; in any case it should ensure a fine distribution of the active ingredient.

For the preparation of solutions to be sprayed direct, hydrocarbon having boiling points higher than 150°C, e.g. tetrahydronaphthalene or alkylated naphthalenes, or organic liquids having boiling points higher than 150°C and having one or more than one functional group, e.g. the keto group, the ether group, the ester group or the amide group, this group or these groups being attached as substituent(s) to a hydrocarbon chain or being a component of a heterocyclic ring, may be used as spray liquids.

Aqueous formulations may be prepared from emulsion concentrates, pastes or wettable powders by adding water. To prepare emulsions the ingredients as such or dissolved in a solvent may be homogenized in water or organic solvents by means of wetting or dispersing agents, e.g. polyethylene oxide adducts. Concentrates which are suitable for dilution with water may be prepared from active ingredient, emulsifying or dispersing agent and possibly solvent.

Dusts may be prepared by mixing or grinding the active ingredients with a solid carrier, e.g. kieselguhr, talc, clay or fertilizers.

The following examples illustrate the application of the pesticides.

For these experiments, the following known insecticidal active ingredients are employed for comparison purposes:

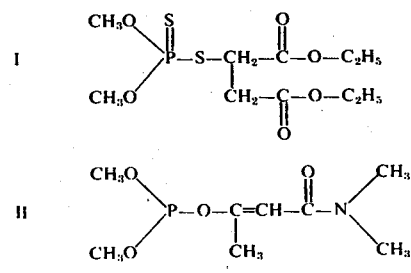

III  (U.S. Patent No. 2,891,887)

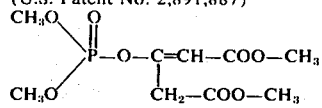

IV  (British Patent No. 1,062,952)

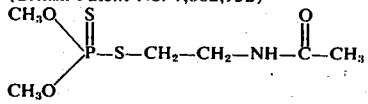

EXAMPLE 3

Application test with houseflies (Musca domestica)

1 mm$^3$ of an acetonic solution of the action ingredients is applied to the ventral abdomen of houseflies under $CO_2$ narcosis. The mortality rate, from which the $LD_{50}$ ($1\gamma = 1 \times 10^{-6}$ g) is calculated, is determined after 4 hours.

| | | |
|---|---|---|
| Known active ingredient I | $LD_{50}$ | 0.6 γ/fly |
| Known active ingredient II | $LD_{50}$ | 0.8 γ/fly |
| Known active ingredient IV | | 10.0 γ/fly ineffective |
| New active ingredient | | |
| (see table above)  No. 1 | $LD_{50}$ | 0.033 γ/fly |
| No. 4 | $LD_{50}$ | 0.18 γ/fly |
| No. 5 | $LD_{50}$ | 0.18 γ/fly |
| No. 27 | $LD_{50}$ | 0.4 γ/fly |
| No. 40 | $LD_{50}$ | 0.3 γ/fly |

EXAMPLE 4

Continuous contact with houseflies (Musca domestica)

The inside of Petri dishes 10 cm in diameter is wetted with an acetonic solution of the active ingredients. After the solvent has evaporated, 4 day old houseflies are placed in the dishes. The mortality rate is determined after 4 hours.

| | | |
|---|---|---|
| Known active ingredient I | | 0.2 mg/dish effective |
| New active ingredient | No. 1 | 0.02 mg/dish effective |
| | No. 2 | 0.02 mg/dish effective |
| | No. 3 | 0.05 mg/dish effective |
| | No. 5 | 0.02 mg/dish effective |
| | No. 6 | 0.02 mg/dish effective |
| | No. 7 | 0.02 mg/dish effective |
| | No. 8 | 0.02 mg/dish effective |
| | No. 9 | 0.02 mg/dish effective |
| | No. 10 | 0.02 mg/dish effective |
| | No. 11 | 0.02 mg/dish effective |
| | No. 12 | 0.002 mg/dish effective |
| | No. 13 | 0.02 mg/dish effective |
| | No. 14 | 0.02 mg/dish effective |
| | No. 15 | 0.02 mg/dish effective |
| | No. 16 | 0.02 mg/dish effective |
| | No. 18 | 0.02 mg/dish effective |
| | No. 27 | 0.02 mg/dish effective |
| | No. 31 | 0.02 mg/dish effective |
| | No. 32 | 0.02 mg/dish effective |
| | No. 33 | 0.02 mg/dish effective |
| | No. 37 | 0.02 mg/dish effective |

EXAMPLE 5

Action on red spider mite (Tetranychus telarius)

Bean plants severely attacked by red spider mites are sprayed with aqueous solutions of the active ingredients until they are dripping wet. The action of the ingredients is determined after 1 week.

| | |
|---|---|
| Known active ingredient II | 0.05% mortality greater than 90% |
| Known active ingredient III | 0.1% mortality greater than 90% |
| New active ingredient  No. 1 | 0.025% mortality greater than 90% |
| No. 4 | 0.01% mortality greater than 90% |
| No. 5 | 0.025% mortality greater than 90% |
| No. 17 | 0.025% mortality greater than 90% |
| No. 18 | 0.025% mortality greater than 90% |
| No. 19 | 0.01% mortality greater than 90% |
| No. 20 | 0.01% mortality greater than 90% |
| No. 21 | 0.025% mortality greater than 90% |
| No. 22 | 0.01% mortality greater than 90% |
| No. 23 | 0.025% mortality greater than 90% |
| No. 24 | 0.025% mortality greater than 90% |
| No. 25 | 0.04% mortality greater than 90% |
| No. 26 | 0.025% mortality greater than 90% |
| No. 27 | 0.025% mortality greater than 90% |
| No. 28 | 0.025% mortality greater than 90% |
| No. 29 | 0.01% mortality greater than 90% |
| No. 30 | 0.025% mortality greater than 90% |
| No. 31 | 0.025% mortality greater than 90% |
| No. 33 | 0.025% mortality greater than 90% |
| No. 34 | 0.01% mortality greater than 90% |
| No. 35 | 0.025% mortality greater than 90% |
| No. 36 | 0.025% mortality greater than 90% |
| No. 37 | 0.025% mortality greater than 90% |
| No. 38 | 0.025% mortality greater than 90% |
| No. 39 | 0.025% mortality greater than 90% |
| No. 41 | 0.025% mortality greater than 90% |

EXAMPLE 6

Systemic action on bean aphids (Aphis fabae)

Bean aphids (Aphis fabae) are placed on young bean plants (Vicia faba) in pots filled with humus garden soil. After 7 days, the plants are treated with 20 ml of the aqueous formulations of the active ingredients. The mortality rate of the bean aphids is determined after 48 hours.

| | |
|---|---|
| Known active ingredient I | 0.1% (by weight) ineffective |
| New active ingredient  No. 17 | 0.05% 80% mortality |
| No. 18 | 0.01% mortality greater than 90% |
| No. 19 | 0.02% mortality greater than 90% |
| No. 20 | 0.04% mortality greater than 90% |
| No. 21 | 0.05% 80% mortality |
| No. 23 | 0.02% mortality greater than 90% |
| No. 24 | 0.01% mortality greater than 90% |
| No. 26 | 0.05% mortality greater than 90% |
| No. 28 | 0.05% mortality greater than 90% |
| No. 29 | 0.01% mortality greater than 90% |
| No. 32 | 0.05% mortality greater than 90% |
| No. 33 | 0.05% mortality greater than 90% |
| No. 35 | 0.05% mortality greater than 90% |
| No. 39 | 0.05% mortality greater than 90% |
| No. 41 | 0.01% mortality greater than 90% |

EXAMPLE 7

60 parts by weight of compound 1 is mixed with 40 parts by weight of N-methyl-α-pyrrolidone. A mixture is obtained which is suitable for application in the form of very fine drops.

EXAMPLE 8

20 parts by weight of compound 2 is dissolved in a mixture consisting of 80 parts by weight of xylene, 10 parts by weight of the adduct of 8 to 10 moles of ethylene oxide to 1 mole of oleic acid-N-monoethanolamide, 5 parts by weight of the calcium salt of dodecylbenzenesulfonic acid, and 5 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 9

20 parts by weight of compound 3 is dissolved in a mixture consisting of 40 parts by weight of cyclohexanone, 30 parts by weight of isobutanol, 20 parts by weight of the adduct of 7 moles of ethylene oxide to 1 mole of isooctylphenol, and 10 parts by weight of the adduct of 40 moles of ethylene oxide to 1 mole castor oil. By pouring the solution into 100,000 parts by weight of water and uniformly distributing it therein, an aqueous dispersion is obtained containing 0.02% by weight of the active ingredient.

EXAMPLE 10

20 parts by weight of compound 4 is dissolved in a mixture consisting of 25 parts by weight of cyclohexanol, 65 parts by weight of a mineral oil fraction having a boiling point between 210° and 280°C, and 10 parts by weight of the adduct of 40 moles of ethylene oxide to 1 mole of castor oil. By pouring the solution into 100,000 parts by weight of water and uniformly distributing it therein, an aqueous dispersion is obtained containing 0.02% by weight of the active ingredient.

EXAMPLE 11

20 parts by weight of compound 5 is well mixed with 3 parts by weight of the sodium salt of diisobutylnaphthalene-α-sulfonic acid, 17 parts by weight of the sodium salt of a ligninsulfonic acid obtained from a sulfite waste liquor, and 60 parts by weight of powdered silica gel, and triturated in a hammer mill. By uniformly distributing the mixture in 20,000 parts by weight of water, a spray liquid is obtained containing 0.1% by weight of the active ingredient.

EXAMPLE 12

3 parts by weight of compound 6 is intimately mixed with 97 parts by weight of particulate kaolin. A dust is obtained containing 3% by weight of the active ingredient.

EXAMPLE 13

30 parts by weight of compound 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

We claim:

1. A dithophosphoric ester having the formula

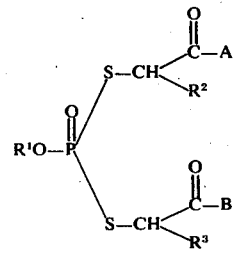

wherein:
$R^1$ is methyl or ethyl;
A is $NHCH_3$;
B is $NHCH_3$ or $NH_2$;
$R^2$ is hydrogen; and
$R^3$ is hydrogen or methyl.

2. The compound of the formula

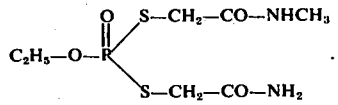

* * * * *